(12) United States Patent
Mahanthappa et al.

(10) Patent No.: US 9,440,905 B2
(45) Date of Patent: Sep. 13, 2016

(54) POLYMERIZABLE GEMINI DICARBOXLATE SURFACTANTS AND LYOTROPIC LIQUID CRYSTALS AND MEMBRANES MADE THEREFROM

(71) Applicant: Wisconsin Alumni Research Foundation, Madison, WI (US)

(72) Inventors: Mahesh Kalyana Mahanthappa, Madison, WI (US); Gregory Paul Sorenson, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 540 days.

(21) Appl. No.: 13/747,865

(22) Filed: Jan. 23, 2013

(65) Prior Publication Data

US 2013/0190417 A1 Jul. 25, 2013

Related U.S. Application Data

(60) Provisional application No. 61/589,574, filed on Jan. 23, 2012.

(51) Int. Cl.
| | | |
|---|---|---|
| *C07C 57/13* | (2006.01) | |
| *C09K 19/02* | (2006.01) | |
| *C07C 309/15* | (2006.01) | |
| *C09K 19/04* | (2006.01) | |
| *C09K 19/52* | (2006.01) | |

(52) U.S. Cl.
CPC ............. *C07C 57/13* (2013.01); *C07C 309/15* (2013.01); *C09K 19/0283* (2013.01); *C09K 2019/0448* (2013.01); *C09K 2019/528* (2013.01)

(58) Field of Classification Search
CPC .......................... C09K 19/0283; C07C 57/13
See application file for complete search history.

(56) References Cited

U.S. PATENT DOCUMENTS

| | | | |
|---|---|---|---|
| 6,046,292 | A | 4/2000 | Lochhead et al. |
| 7,090,788 | B2 | 8/2006 | Elliott |
| 7,604,129 | B2 | 10/2009 | Gin et al. |
| 2004/0211939 | A1 | 10/2004 | Elliott |
| 2006/0096922 | A1 | 5/2006 | Gin et al. |
| 2007/0218371 | A1 | 9/2007 | Elliott et al. |
| 2008/0029735 | A1 | 2/2008 | Gin et al. |
| 2008/0089924 | A1 | 4/2008 | Nojima et al. |

(Continued)

FOREIGN PATENT DOCUMENTS

WO 2004060531 A1 7/2004

OTHER PUBLICATIONS

Sorenson, G.P.; Coppage, K.L.; Mahanthappa, M.K. "Unusually Stable Aqueous Lyotropic Gyroid Phases from Gemini Dicarboxylate Surfactants" J. Am. Chem. Soc., 2011.*

(Continued)

*Primary Examiner* — Mike M Dollinger
*Assistant Examiner* — Christina Wales
(74) *Attorney, Agent, or Firm* — Cantor Colburn LLP (57) ABSTRACT

The disclosure provides anionic Gemini surfactants comprising at least two carbonyl moieties and at least two aliphatic moieties. In some aspects, at least two of the aliphatic moieties comprise at least seven carbon atoms and at least one pair of conjugated carbon-to-carbon double bonds. The anionic Gemini surfactants are polymerizable and may be used to prepare triply periodic multiply continuous lyotropic phase and polymers thereof that substantially retain triply periodic multiply continuous lyotropic phase structure.

4 Claims, 4 Drawing Sheets (56) References Cited

U.S. PATENT DOCUMENTS

| | | |
|---|---|---|
| 2009/0173693 A1 | 7/2009 | Gin et al. |
| 2010/0075195 A1 | 3/2010 | Elliott et al. |
| 2012/0211424 A1 | 8/2012 | Gabriel et al. |
| 2013/0190417 A1 | 7/2013 | Mahanthappa et al. |

OTHER PUBLICATIONS

Hoag, B.P.; Gin, D.L. "Cross-Linkable Liquid Crystal Monomers Containing Hydrocarbon 1,3-Diene Tail Systems" Macromolecules. 2000, 33, 8549-8558.*

U.S. Appl. No. 13/472,817, filed May 16, 2012; Non-final Office Action; mailed Feb. 13, 2014; 14 pages.

Heathcock et al.; "Daphniphyllum Alkaloids. 12. A Proposed Biosynthesis of the Pentacyclic Skeleton. proto-Daphniphylline"; J. Org. Chem.; 57; pp. 2554-2566; (1992).

International Search Report and Written Opinion; International Application No. PCT/US2013/022701; International Filing Date Jan. 23, 2013; Date of Mailing Apr. 9, 2013; 16 pages.

Kotha et al.; "Diversity-Oriented Approach to Macrocyclic Cyclophane Derivatives via Ring-Closing Metathesis"; Synlett; 23; pp. 2183-2188; (2012).

Tolstikov et al.; "Telomerization of Butadiene and Isoprene With Sulfones Containing Active Methine and Methylene Groups, Catalyzed by Palladium Complexes"; Bulletin of the Academy of Sciences of the USSR, Division of Chemical Science; 32(3); pp. 529-536; (1983).

Ulrich et al.; "Simple and High Yield Synthesis of (±)10,10'-dimethyl-dotriacontan-1,1'-diol as a Building Block for Branched Bola Compounds. Preparation of (±)10,10'-dimethyl-dotriaconta-1,1'-diyl-bis[2-(trimetylammino)ethyl phosphate] and the Corresponding Unbranched Equivalent"; Chemistry and Physics of Lipids; 90; pp. 25-30; (1997).

Alami et al.; "Alkanediyl-Alpha, Omega-Bis(Dimethylalkylammonium Bromide) Surfactants. 2. Structure of the Lyotropic Mesophases in the Presence of Water"; Langmuir; 9; pp. 940-944; (1993).

Brun et al.; "The Fraction of Associated Counterions and Singly Dispersed Amphiphiles in Micellar Systems from Ion-Exchange Membrane Electrode Measurements"; J. Colloid Interfac. Sci.; 63; pp. 590-592; (1978).

Diamant et al.; Chapter 3, "Models of Gemini Surfactants" in Surfactant Science Series, Zana, R., Ed.; Marcel Dekker, Inc., New York; pp. 37-64; (2004).

Dix et al.; "Lyotropic and Interfacial Behavior of an Anionic Gemini Surfactant"; J. Colloid Interfac. Sci.; 296; pp. 762-765; (2006).

Fairhurst et al.; Chapter 7, "Lyotropic Surfactant Liquid Crystals"; in Handbook of Liquid Crystals, Dietrich Demus , Editor; Wiley-VCH, vol. 3; pp. 341-392; (1998).

Han et al.; "A Tri-Continuous Mesoporous Material With a Silica Pore Wall Following a Hexagonal Minimal Surface"; Nature Chem; 1; pp. 123-127; (2009).

Hentze et al.; "Lyotropic Mesophases of Poly(ethylene oxide)-b-poly(butadiene)Diblock Copolymers and Their Cross-Linking to Generate Ordered Gels"; Macromolecules; 32; pp. 5803-5809; (1999).

Hoag et al.; "Cross-Linkable Liquid Crystal Monomers Containing 1,3-Diene Tail Systems"; Macromolecules; 33(23); pp. 8549-8558; (2000).

Israelachvili, J. N., Chapter 17, "Aggregation of Amphiphilic Molecules into Micelles, Bilayers, Vessicles, and Biological membranes"; Intermolecular and Surface Forces, 2nd ed.; Academic Press London ; 367-395; (1991).

Johansson et al.; "Membrane Protein Crystallization From Lipidic Phases"; Curr. Opin. Struct. Biol.; 19; pp. 372-378; (2009).

Leal et al.; "Highly Efficient Gene Silencing Activity of siRNA Embedded in a Nanostructured Gyroid Cubic Lipid Matrix"; J. Am. Chem. Soc.; 132; pp. 16841-16847; (2010).

Matsen et al.; "Origins of Complex Self-Assembly in Block Copolymers"; Macromolecules; 29; pp. 7641-7644; (1996).

Menger et al.; "Gemini Surfactants"; Angew. Chem. Int. Ed.; 39; pp. 1906-1920; (2000).

Pfeffer et al.; "Alpha Anions of Carboxylic-Acids. 2. Formation and Alkylation of Alpha-Metalated Aliphatic Acids"; Journal of Organic Chemistry; 37; pp. 451-458; (1972).

Pindzola et al.; "Lyotropic Liquid-Crystalline Phase Behavior of Some Alkyltrimethylphosphonium Bromides"; Langmuir; 16; pp. 6750-6753; (2000).

Pindzola et al.; "Cross-Linked Normal Hexagonal and Bicontinuous Cubic Assemblies Via Polymerizable Gemini Amphiphiles"; J. Am. Chem. Soc.; 125; pp. 2940-2949; (2003).

Rummel et al.; "Lipidic Cubic Phases: New Matrixes for the Three-Deimensional Crystallization of Membrane Proteins"; J. Struct. Biol.; 121; pp. 82-91; (1998).

Seddon, J. M.; "Structure of the Inverted Hexagonal (HII) Phase, and Non-Lamellar Phase Transitions of Lipids"; Biochim. Biophys. Acta; 1031; pp. 1-69; (1990).

Shearman et al.; "Calculations of and Evidence for Chain Packing Stress in Inverse Lyotropic Bicontinuous Cubic Phases"; Langmuir; 23; pp. 7276-7285; (2007).

Shearman et al.; "Ordered Micellar and Inverse Micellar Lyotropic Phases"; Liq. Cryst.; 37; pp. 679-694; (2010).

Svenson S.; "Self-assembly and Self-organization: Important Processes, but Can We Predict Them?"; J. Disper. Sci. Tech.; 25; pp. 101-118; (2004).

Gin et al.; "Polymerized Lyotropic Liquid Crystal Assemblies for Membrane Applications"; Macromol. Rapid Commun.; 29; pp. 367-389; (2008).

Hatakeyama et al.; "Nanoporous, Bicontinuous Cubic Lyotropic Liquid Crystal Networks Via Polymerizable Gemini Ammonium Surfactants"; with Abstract; Chem. Matter.; 22(16); pp. 4525-4527; (2010).

Hyde, Stephen T.; "Identification of Lyotropic Liquid Crystalline Mesophases"; from Chapter 16, Handbook of Applied Surface and Colloid Chemistry; vols. 1-2; John Wiley & Sons; pp. 299-332; (2002).

Kato et al.; "Functional Liquid-Crystalline Assemblies: Self-Organized Soft Materials"; Angew. Chem. Int. Ed.; 45; pp. 38-68; (2006).

Kerr et al.; "New Type of Li Ion Conductor With 3D Interconnected Nanopores Via Polymerization of a Liquid Organic Electrolyte-Filled Lyotropic Liquid-Crystal Assembly"; J. Am. Chem. Soc.; 131; pp. 15972-15973; (2009).

Sorenson et al.; "Unusually Stable Aqueous Lyotrophic Gyroid Phases from Gemini Dicarboxylate Surfactants"; J Am. Chem. Soc.; 133; pp. 14928-14931; (2011).

Zhou et al.; "New Type of Membrane Material for Water Desalination Based on a Cross-Linked Bicontinuous Cubic Lyotropic Liquid Crystal Assembly"; J. Am. Chem. Soc.; 129; pp. 9574-9575; (2007).

Wang et al.; "Structural Effect of Thiol-Compounds on the Thiol-ene Based UV Curable Adhesive"; Appled Mechanics and Materials; 469; pp. 162-166; (2014).

* cited by examiner

POLYMERIZABLE GEMINI DICARBOXLATE SURFACTANTS AND LYOTROPIC LIQUID CRYSTALS AND MEMBRANES MADE THEREFROM

REFERENCE TO CROSS-RELATED APPLICATIONS

This application claims priority to U.S. Provisional Application 61/589,574 filed on Jan. 23, 2012, which is incorporated herein by reference in its entirety.

FIELD OF THE DISCLOSURE

The field of the disclosure relates generally to polymerizable Gemini surfactants and polymers and lyotropic liquid crystals prepared therefrom.

BACKGROUND

Aqueous lyotropic liquid crystal (LLC) assemblies have garnered widespread attention in disparate areas of chemistry, by virtue of their utility in highly selective chemical separations such as water desalination and selective ion-transporting membranes, as templates for mesoporous inorganic materials, as media for biophysical studies of trans-membrane proteins ("cubic lipidic phases"), and as therapeutic nucleic acid delivery vehicles. LLCs form by the concentration-dependent supramolecular self-organization of amphiphilic molecules in water into soft materials having distinct hydrophilic and hydrophobic nanoscale domains (approximately 7 to 100 Å) with long-range periodic order. LLCs typically exhibit ordered phases such as lamellae ($L_\alpha$), bicontinuous cubic (Q; e.g., double gyroid, double diamond, and "Plumber's Nightmare"), hexagonally packed cylinders (H), and discontinuous cubic (I; e.g., body-centered cubic) morphologies. High symmetry Q-phase assemblies, exemplified by the gyroid (G) phase, are particularly desirable for membrane applications by virtue of their interpenetrating aqueous and hydrophobic domains with tunable nanopore diameters (approximately 7 to 50 Å) and well-defined nanopore functionalities that percolate over macroscopic length-scales. Q-phases typically exist only in limited water concentration and temperature phase windows, due to the fact that their interfaces substantially deviate from a constant mean interfacial curvature. While "critical packing parameter" models enable correlations of amphiphile structure with the formation of constant mean curvature $L_\alpha$, H, and I phases, these models fail to provide reliable and general molecular design criteria for amphiphiles that form non-constant mean curvature Q phases. It was recently reported that small molecule quaternary ammonium, phosphonium, and imidazolium Gemini amphiphiles, derived from dimerizing single-tail surfactants with an alkyl spacer through the ionic headgroup, exhibit a greater tendency to form G phase LLCs. The notion that Gemini architectures universally form bicontinuous cubic LLC morphologies remains an untested amphiphile design principle.

In order to advance applications of LLC assemblies for membrane filtration, ion conduction, and other transport processes, increased attention has been devoted to polymerizable triply periodic multiply continuous LLCs. The weak non-covalent forces stabilizing these supramolecular assemblies render them soft and mechanically inferior. Also, their concentration dependent phase behavior limits their potential utility in solution-phase molecular sieving for aqueous separations. By installing polymerizable functionalities in the surfactant structure, a LLC assembly may be covalently fixed in place by thermal or photo-polymerization to yield a robust polymeric network with retention of the triply periodic structure. The low dimensionality of $L_\alpha$-phases and H-phases requires domain alignment at macroscopic length-scales in order to achieve transport through either the hydrophilic or hydrophobic domains of an LLC. However, the high symmetry and three-dimensional structural periodicity of the interpenetrating domains of triply periodic multiply continuous phases result in percolating domains that do not require alignment. By virtue of their construction, the hydrophilic and hydrophobic domains of LLCs have dimensions d of approximately 5-100 Å with domain interfaces that are decorated with well-defined chemical functionalities. The dimensions of the water-filled channels are approximately one order of magnitude smaller than those in nanoporous block copolymers (d approximately 50-1000 Å), enabling applications including water desalination, ultrafiltration, selective ion transport.

What is needed are additional molecules that can assemble to form LLC assemblies.

SUMMARY

Briefly, therefore, the present disclosure is directed to a polymerizable molecule having the following structure:

wherein $X_1$ and $X_2$ are each independently an optionally substituted branched, unbranched, or cyclic aliphatic group having from four to 30 carbon atoms;

$Z_1$ and $Z_2$ are integers, each independently having a value of zero, one, two, or three;

Y is a covalently bound divalent linker;

$M_1$ and $M_2$ are the same or different and are each independently selected from hydrogen, hydroxyl, —O($C_1$-$C_8$ alkyl)N($CH_3$)$_3^+$($X^-$) where $X^-$ is a counterion, —($C_0$-$C_8$ alkyl)N$R_{11}R_{12}$, —O($C_1$-$C_8$ alkyl)N$R_{11}R_{12}$, —NH($C_1$-$C_8$ alkyl)N$R_{11}R_{12}$, —NH(CH—$R_{13}$)COOH, —O$R_{11}$, —N$R_{11}R_{14}$, and —O$^-$($M^+$) where $M^+$ is a counterion, wherein $R_{11}$, $R_{12}$, and $R_{14}$ are independently chosen from hydrogen and optionally substituted $C_1$-$C_8$ alkyl, and wherein $R_{13}$ is an amino acid side chain;

and $R_1$ through $R_{10}$ are each independently selected from hydrogen, fluoride, chloride, bromide, $C_1$-$C_8$ alkyl, $C_2$-$C_8$ alkenyl, tri($C_1$-$C_4$ alkyl)silyl, and substituted or unsubstituted phenyl.

In certain embodiments $R_{11}$ and $R_{14}$ are $C_1$-$C_8$ alkyl substituted with at least one substituent chosen from hydroxyl, —SO$_3$H, —OSO$_3$H, and —PO$_3$H, resulting in an $M_1$ or $M_2$ group that is, for example, —OCH$_2$CH(OH)CH$_2$OH, —NH($C_1$-$C_8$ alkyl)SO$_3$H, —N(CH$_3$)($C_1$-$C_8$ alkyl)SO$_3$H, —O($C_1$-$C_8$alkyl)SO$_3$H, —NH($C_1$-$C_8$ alkyl)OSO$_3$H, —N(CH$_3$)(C$_1$-C$_8$ alkyl)OSO$_3$H, —O(C$_1$-C$_8$alkyl)OSO$_3$H, —NH(C$_1$-C$_8$ alkyl)PO$_3$H$_2$, —N(CH$_3$)(C$_1$-C$_8$alkyl)PO$_3$H$_2$, or —O(C$_1$-C$_8$ alkyl)PO$_3$H$_2$.

The disclosure is further directed to a method of preparing a Gemini surfactant. The method comprises (a) contacting a carboxylic acid, a carboxylate salt, or a carboxylate ester with a quantity of a base to thereby deprotonate the alpha carbon of the carboxylic acid, a carboxylate salt, or a carboxylate ester, wherein the carboxylic acid, a carboxylate salt, or a carboxylate ester comprises at least seven carbon atoms and at least one carbon-to-carbon double bond; and (b) contacting the alpha carbon-deprotonated carboxylic acid, a carboxylate salt, or a carboxylate ester with a compound having the structure:

wherein L$_1$ and L$_2$ comprise leaving groups, Y comprises a covalently bound divalent linker, whereby said contact forms the Gemini surfactant.

The disclosure is still further directed to a method of preparing a Gemini surfactant comprising a terminal diene. The method comprises contacting a Gemini dicarboxylate compound with an oxidizing agent to thereby prepare a Gemini dialdehyde; and contacting the Gemini dialdehyde with an (1-trialkylsilyl)allyl-3-boronic acid or an ester thereof, which contact is followed by silanol elimination reaction with an acid or a base to thereby prepare the Gemini surfactant comprising the terminal diene.

The disclosure is still further directed to a method of preparing a polymer. The method comprises contacting an anionic Gemini surfactant with a polymerization initiator to thereby prepare the polymer, wherein the anionic Gemini surfactant comprises at least two carboxylate moieties and at least two aliphatic moieties, wherein at least two of the aliphatic moieties comprise at least seven carbon atoms and at least one pair of conjugated carbon-to-carbon double bonds.

The disclosure is still further directed to a polymer comprising a polymerized anionic Gemini surfactant; wherein the polymerized anionic Gemini surfactant is polymerized from an anionic Gemini surfactant comprising at least two carboxylate moieties and at least two aliphatic moieties, wherein at least two of the aliphatic moieties comprise at least seven carbon atoms and at least one pair of conjugated carbon-to-carbon double bonds.

DETAILED DESCRIPTION

Figure 1A:
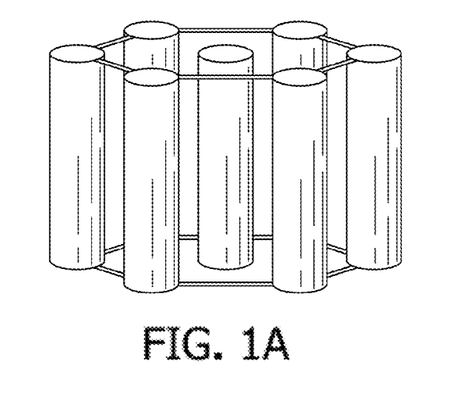
FIGS. 1A through 1F are illustrations of the observed LLC morphologies formed by Gemini surfactants: hexagonal (H$_I$) with constant positive mean curvature (FIG. 1A), lamellar (L$_\alpha$) with flat interfaces (FIG. 1B), Gyroid (G$_I$) (FIG. 1C), Double Diamond (D$_I$) (FIG. 1D), Primitive (P$_I$) (FIG. 1E), and tetracontinuous hexagonal (FIG. 1F) that require substantial positive and negative deviations from constant mean curvature.
Figure 1B:
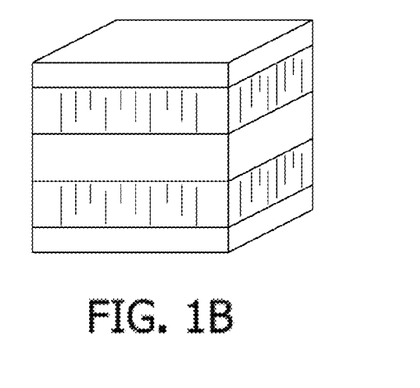
Figure 1C:
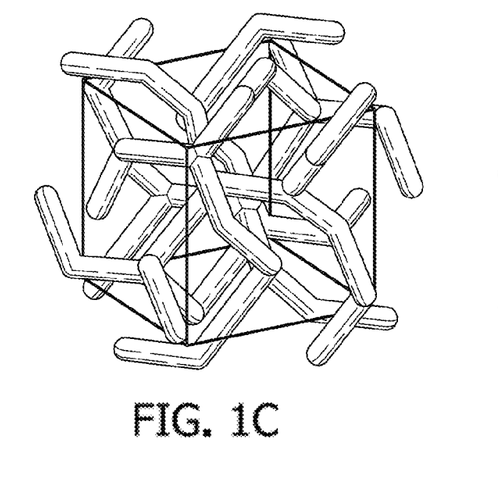
Figure 1D:
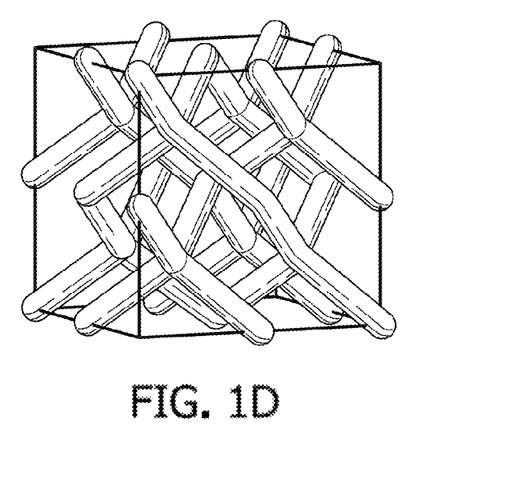
Figure 1E:
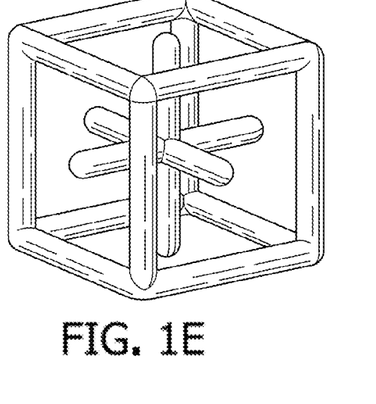
Figure 1F:
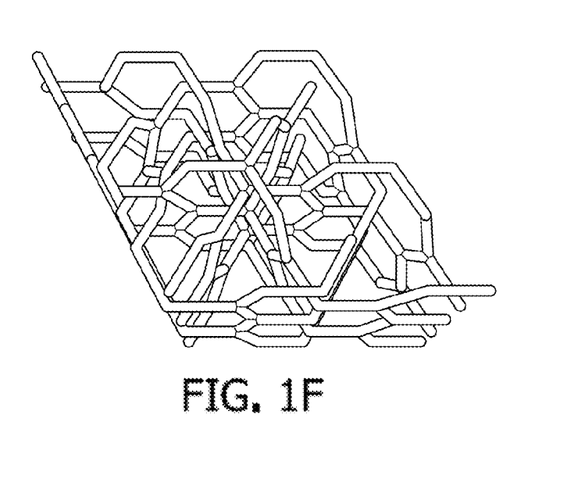

The present disclosure is directed to novel polymerizable Gemini surfactants that can form lyotropic liquid crystals. Lyotropic liquid crystals are comprised of materials that form phases having long-range translational order induced by the addition of a solvent. Stated another way, lyotropic liquid crystals include ordered phases in solvent, in which the structurally periodic phase that exists in the liquid crystal composition varies as a function of concentration of the surfactant in the solvent system, temperature, and pressure. A subset of these phases can be described as being triply periodic, since the phases comprise structures that repeat in three dimensions. LLC phases may be described in a phase diagram in which the X-axis (abscissa) is concentration and the Y-axis (ordinate) is temperature. The liquid crystalline phase that generally forms at low surfactant concentrations is the "micellar cubic" or "discontinuous cubic" phase comprising spherical micelles and which may be denoted by the symbol I$_I$. This is a viscous, optically non-birefringent phase in which the micelles are arranged on a cubic lattice. At higher concentrations, in general, the cylindrical micelles of indefinite length form and are arranged on a two-dimensional hexagonal lattice with long-range periodic order. This lyotropic liquid crystalline phase is known as the "hexagonal phase", or more specifically the "normal" hexagonal phase and is generally denoted by the symbol H$_I$. At higher concentrations, the "lamellar phase" generally forms. This phase is denoted by the symbol L$_\alpha$. This phase consists of surfactant molecules arranged in bilayer sheets separated by layers of solvent. Some materials may form an intermediate phase at concentrations generally between those concentrations at which hexagonal and lamellar phases form. Some intermediate phases may be referred to as bicontinuous cubic phases or Q-phases. Bicontinuous cubic phases include gyroid phase (G$_I$, space group #230), the double diamond phase (space group #224), and the primitive cubic phase (space group #229). See FIGS. 1A through 1F. FIGS. 1A through 1F depicts the Hexagonal (H$_I$) (FIG. 1A), Lamellar (L$_\alpha$) (FIG. 1B), and Gyroid (G$_I$) (FIGS. 1C through 1E) phases. FIG. 1F depicts a tetracontinuous hexagonal phase, which may be prepared using anionic Gemini surfactants of the present disclosure. The various phases that a lyotropic liquid crystal may assume are generally discussed as a function of concentration; however, phase transitions may occur as the temperature or pressure of the system increases. Surfactant concentrations at which a gyroid phase, for example, may form at lower temperatures, e.g., 20° C., may shift or the range may narrow as the temperature of the system increases, e.g., to 100° C.

The present disclosure is directed to polymerizable anionic Gemini surfactants comprising at least one carboxylate moiety, preferably two carboxylate moieties, that robustly form lyotropic liquid crystals upon the addition of a solvent. The polymerizable anionic Gemini surfactants of the present disclosure form triply periodic multiply continuous lyotropic phases over broad ranges of concentration and temperature. These triply periodic multiply continuous phases encompass bicontinuous cubic phases, for example, the gyroid phase (space group #230), double diamond phase (space group #224), or primitive cubic phase (space group #229). The triply periodic multiply continuous phases of the present disclosure additionally encompass tetracontinuous phases, such as a novel hexagonal tetracontinuous phase (space group #193) with percolating pores in three dimensions. This phase is comprised of three distinct, interpenetrating, and unconnected hydrophobic networks each having $P6_3/mmc$ (space group #194) symmetry to yield an overall hydrophobic network structure with $P6_3/mcm$ symmetry (space group #193), in which the voids are filled with solvent. This tetracontinuous phase is related yet distinct from that described previously in mesoporous silicates.

The polymerizable anionic Gemini surfactants of the present disclosure are particularly useful for membrane applications of lyotropic liquid crystals since the surfactants are capable of being chemically fixed in place by crosslinking polymerization, e.g., chemical crosslinking polymerization, to form mechanically robust membranous materials. Such mechanically robust materials may find particular use in separations, catalysis, and selective ion transport.

The polymerizable anionic Gemini surfactants additionally comprise multiple, preferably two, hydrophobic tail groups, the tail groups being linked via a covalently bound divalent linker, Y, generally bonded to the alpha carbon of the carboxylic acids. A polymerizable anionic Gemini surfactant according to the present disclosure has the following structure (I):

In structure (I), $X_1$ and $X_2$ are each independently an optionally substituted branched, unbranched, or cyclic aliphatic group having from four to 30 carbon atoms, specifically from four to 20 carbon atoms, even more specifically from four to 16 carbon atoms, such as from four to nine carbon atoms. The $X_1$ and $X_2$ aliphatic groups may be saturated or may comprise unsaturated moieties, such as alkenyl or alkynyl. That is, the $X_1$ and $X_2$ aliphatic groups may comprise one or more carbon-to-carbon double bonds and/or one or more carbon-to-carbon triple bonds. Additionally, the $X_1$ and $X_2$ aliphatic groups may comprise cyclic moieties, i.e., cycloalkyl, either within the main carbon chain or branched therefrom. The $X_1$ and $X_2$ aliphatic groups may comprise branching moieties, e.g., alkyl, alkenyl, trialkylsilyl, phenyl, and substituted phenyl. The $X_1$ and $X_2$ aliphatic groups may comprise hydrocarbyls (i.e., the entirety of the aliphatic group comprises only carbon-carbon or carbon-hydrogen bonds) or the aliphatic groups may comprise heteroatom substituents, such as halide atoms (e.g., fluoride, chloride, and bromide) bonded to carbon atoms. In some embodiments, the aliphatic groups contain at least two fluoride atoms, such as at least four fluoride atoms. In some embodiments, the aliphatic groups are perfluorinated, meaning that all hydrogen atoms along the carbon chain are replaced with fluoride atoms.

In specific embodiments, the $X_1$ and $X_2$ aliphatic moieties comprise at least one carbon-to-carbon double bond. In other embodiments, each of the $X_1$ and $X_2$ aliphatic moieties comprise at least two carbon-to-carbon double bonds, wherein the carbon-to-carbon double bonds are separated by at least one methylene group, such as one methylene group, two methylene groups, three methylene groups, or more. Anionic Gemini surfactants comprising long, saturated aliphatic chains tend to have a high degree of crystallinity, which may shorten the concentration ranges over which the surfactants form triply periodic multiply continuous phases. Double bonded moieties advantageously disrupt the crystal-forming tendencies of long aliphatic chain surfactants, thereby extending the triply periodic multiply continuous phase concentration and temperature ranges.

In a specific embodiment, $X_1$ and $X_2$ are both $C_2$ to $C_{20}$ alkyl, specifically $C_2$ to $C_{10}$ alkyl, and more specifically $C_4$-$C_7$ alkyl, any of $C_4$, $C_5$, $C_6$, or $C_7$ alkyl.

In structure (I), $Z_1$ and $Z_2$ are integers, each independently having a value of zero, one, two, or three. In specific embodiments of the present disclosure, $Z_1$ and $Z_2$ are each independently zero or one. In some embodiments of the present disclosure, $Z_1$ and $Z_2$ are both one.

In structure (I), $R_1$ through $R_{10}$ are each independently selected from the group consisting of hydrogen, fluoride, chloride, bromide, $C_1$ to $C_8$ alkyl, $C_2$ to $C_8$ alkenyl, tri($C_1$-$C_4$ alkyl)silyl, and substituted or unsubstituted phenyl. In one embodiment, the alkyl and alkenyl moieties have 1 to 4 carbon atoms. Trialkylsilyl has the general structure $R_3Si$, wherein the R is selected from methyl, ethyl, propyl, isopropyl, butyl, sec-butyl, tert-butyl, and combinations thereof. In some embodiments, each of $R_1$ through $R_{10}$ is independently chosen from hydrogen and halogen. In certain embodiments each of $R_1$ through $R_{10}$ is hydrogen. In embodiments wherein the $X_1$ and $X_2$ aliphatic moieties are perfluorinated, each of $R_1$ through $R_{10}$ is fluoride.

In structure (I), Y is a covalently bound divalent linker. In some embodiments, Y comprises an optionally substituted $C_1$-$C_{20}$ aliphatic group, an optionally substituted $C_1$-$C_{20}$ heteroaliphatic group, which aliphatic and heteroaliphatic groups may be branched, unbranched, or cyclic.

When Y is an aliphatic group it comprises a group of three carbon atoms to 20 carbon atoms, such as a group of three carbon atoms to 8 carbon atoms. An "aliphatic group" may be saturated or unsaturated hydrocarbon group such as an alkyl, alkenyl or alkynyl group, or a non-aromatic cyclic group, such as a cyclohexane, or may contain both a non-aromatic cyclic group and an acyclic hydrocarbon chain. A "heteroaliphatic group" is an aliphatic group in which one or more carbons in the aliphatic group has been replaced with a heteroatom independently chosen from N, O, S, and P. In some embodiments, Y comprises heteroatoms, such as oxygen, that increase the hydrophilicity of the covalently bound divalent linker, Y. Heteroaliphatic linkers may increase hydrophilicity or alter linker conformations to enable formation of triply periodic multiply continuous phase stabilization with different stabilities. The aliphatic or heteroaliphatic group may be substituted with substituents such as, but not limited to, halogen, hydroxyl, amino, cyano, —CHO, —COOH, alkoxy, alkanoyl, aminoalkyl, alkylcarboxamide, and alkylester.

Figure 2A:
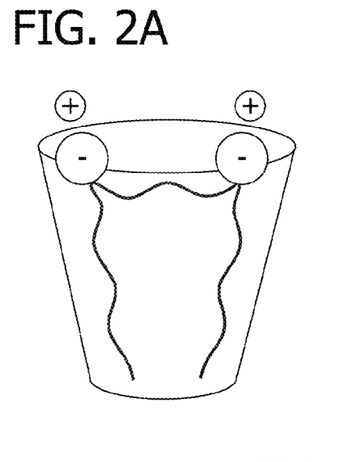
FIGS. 2A through 2C are illustrations of the variety of possible curvatures adopted by Gemini surfactants with flexible hydrophobic alkyl spacers.
Figure 2B:
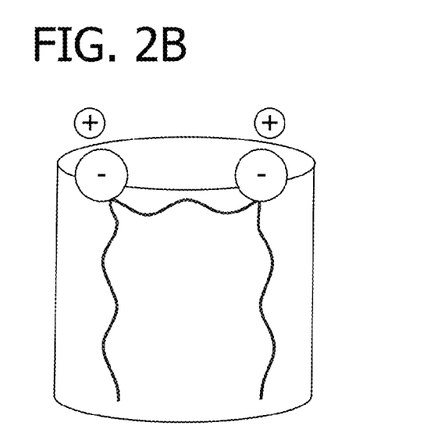
Figure 2C:
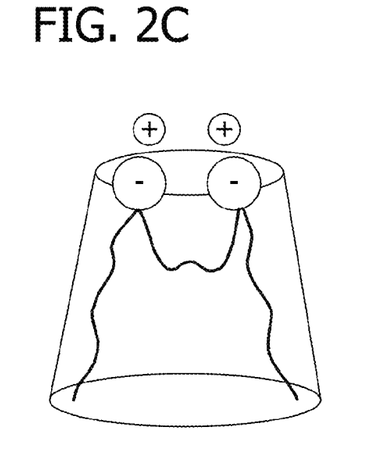

In some specific embodiments, Y comprises an unsubstituted branched or unbranched aliphatic group comprising three to 20 carbon atoms, such as three to 12 carbon atoms, or three to eight carbon atoms. Aliphatic linkers, including acyclic aliphatic linkers provide a large degree of flexibility to the connection. Flexible hydrophobic spacers confer conformational flexibility that enables the surfactant to accommodate the substantial deviations from constant mean interfacial curvature required for triply periodic multiply continuous phase stabilization. See FIGS. 2A through 2C for illustrations of the curvatures afforded by flexible aliphatic connecting moieties, including positive curvature (FIG. 2A), flat curvature (FIG. 2B), and negative curvature (FIG. 2C).

In some embodiments, Y comprises an aryl or heteroaryl group, comprising one aromatic ring or a bi- or tri-cyclic fused rings system of which at least one ring is aromatic, wherein each aromatic ring in the aryl or heteroaryl group contains 5-6 ring atoms, with 0-4 heteroatoms independently chosen from N, O, and S with remaining ring atoms being carbon, and each non-aromatic ring in the aryl or heteroaryl group contain 3-7 ring atoms with 0 to 2 heteroatoms independently chosen from N, O, and S and remaining ring atoms being carbon, and wherein the aryl or heteroaryl group optionally comprises one or two $C_1$-$C_5$ aliphatic chains wherein the point of attachment of Y is a carbon in the $C_1$-$C_5$ aliphatic chain. Rigid hydrophobic spacers alter conformational flexibility that enables formation of triply periodic multiply continuous phase stabilization with different stabilities. Aryl group substituents may include fluoride, chloride, bromide, methyl, ethyl, propyl, butyl hydroxyl, alkoxy generally having from one to four carbon atoms, nitro, and amines having the general structure —$NH_xR$ wherein x has a value from 0 to 2, and R may be an alkyl having from one to four carbon atoms. A heteroaryl group may be for example a pyridyl, pyrazolyl, furanyl pyrrolyl, thienyl, or imidazolyl group. The aliphatic chains extending from the aryl moiety generally have 0 to five carbon atoms, one to five carbon atoms, or one to three carbon atoms. The aliphatic chains may be located ortho, meta, or para to each other around the aromatic ring. In some embodiments, such a connecting moiety has the structure:

wherein $n_1$ and $n_2$ are integers, each having an independent value between 0 and five, between one and five, or between one and three. The aliphatic chains herein may be located ortho, meta, or para to each other around the aromatic ring.

In some embodiments, the hydrophilic moiety comprises a polyalkylether moiety, for example, a short polyethylene oxide or polypropylene oxide, generally having 1 to 4 repeat units.

In one embodiment, the connecting moiety is a poly($C_1$-$C_3$)alkylether moiety having 1 to 4 repeating units. In one embodiment, the hydrophilic moiety has the structure:

wherein $n_3$ is an integer having a value of one to four, such as one or two. This group may be optionally substituted.

In some embodiments, the hydrophilic connecting moiety contains hydroxyl or alkoxy substituents. Such a connecting moiety may have the structure:

wherein $R_{15}$ and $R_{16}$ are each independently hydrogen, hydroxyl, alkyl or alkoxy having from one to five carbon atoms; and $n_4$ is an integer having a value of one to ten, such as one to six, or one to three. One such hydrophilic moiety has the structure:

In further embodiments, linking group Y is

In one embodiment of structure (I), $M_1$ and $M_2$ are each independently a group-$O^-(M)$, where $M^+$ is a counterion, or another covalently bonded group as described herein. Without being held to theory, it is believed that the counterion in the polymerizable anionic carboxylate Gemini surfactants of the present disclosure, when present, also plays a role in enhancing the flexibility and the curvature of the surfactant. Effective charge neutralization through counterion associations with the headgroup allows the alkyl spacer between the carboxylate headgroups to relax, enabling the Gemini surfactant to adopt a wider range of interfacial curvatures over a broader range of headgroup hydration levels to stabilize the non-constant mean curvature $G_I$-phase. Exemplary $M^+$ counterions include among lithium ion; sodium ion; potassium ion; zinc ion; cesium ion; magnesium ion; calcium ion; ammonium ion; alkylammonium ion having the structure $H_xR_{4-x}N^+$ wherein x is an integer having a value of 0 through 4 and R is selected from the group consisting of methyl, ethyl, propyl, butyl, and combinations thereof; tetrakis(hydroxymethyl)phosphonium ion; tetramethylphosphonium ion; choline; imidazolium; bis(quaternary ammonium) ion, and combinations thereof. Alkylammonium ions may include, for example, methylammonium ion, dimethylammonium ion, trimethylammonium ion, ethylammonium ion, diethylammonium ion, triethylammonium ion, tetramethylammonium ion, and tetraethylammonium ion. Specific $M^+$ counterions include sodium ion, potassium ion, and tetramethylammonium ion.

In some embodiments, $M_1$ and $M_2$ are is a covalently bonded group, such as hydrogen, hydroxyl, an optionally substituted alkyl group, an optionally substituted alkoxy group, an optionally substituted mono- or di-alkylamino group, or an optionally substituted (mon- or di-alkylamino) alkyl group. Particular $M_1$ and $M_2$ groups include —NH (CH—$R_{13}$)COOH, in which $R_{13}$ is an amino acid side chain and —NH($C_1$-$C_8$alkyl)$SO_3$H. In some embodiments, $M_1$ or $M_2$ is an aliphatic group, e.g., an alkyl group, having one to eight carbon atoms, or one to four carbon atoms, such as methyl, ethyl, isopropyl, n-propyl, isobutyl, n-butyl, or sec-butyl. In some embodiments, M is methyl. In some embodiments, $M_1$ and $M_2$ are the same or different and are each independently —$O^-(M^+)$ where $M^+$ is a counterion, or a $M_1$ and $M_2$ are a covalently bonded group selected from —($C_1$-$C_8$ alkyl)$NR_{11}R_{12}$—NH(CH—$R_{13}$)COOH, —NH ($C_1$-$C_8$ alkyl)$SO_3$H, or —$OR_{11}$ wherein $R_{11}$ and $R_{12}$ are independently chosen from hydrogen and optionally substituted $C_1$-$C_8$alkyl, and $R_{13}$ is an amino acid side chain. In specific embodiments, $M_1$ and $M_2$ are selected from the group consisting of sodium ions, potassium ions, and tetramethylammonium ions. In more specific embodiments, $M_1$ and $M_2$ are independently selected from the group consisting of hydroxyl, methoxy, —$O^-Na^+$, and —$O^-K^+$.

In some embodiments $M_1$ and $M_2$ are each independently —$O^-(M^+)$ where $M^+$ is a counterion, or $M_1$ and $M_2$ are each independently (i) —O($C_1$-$C_8$ alkyl)N($CH_3$)$_3^+$($X^-$) where $X^-$ is a counterion, —($C_0$-$C_8$ alkyl)$NR_{11}R_{12}$, —O($C_1$-$C_8$ alkyl)$NR_{11}R_{12}$, —NH($C_1$-$C_8$ alkyl)$NR_{11}R_{12}$, —NH(CH—$R_{13}$)COOH, —$OR_{11}$, —$NR_{11}R_{14}$, and —$O^-(M^+)$ where $M^+$ is a counterion, wherein $R_{11}$, $R_{12}$, and $R_{14}$ are independently chosen from hydrogen and optionally substituted $C_1$-$C_8$ alkyl, and wherein $R_{13}$ is an amino acid side chain; or

(ii) —$OCH_2CH(OH)CH_2OH$, —NH($C_1$-$C_8$alkyl)$SO_3$H, —N($CH_3$)($C_1$-$C_8$ alkyl)$SO_3$H, —O($C_1$-$C_8$alkyl)$SO_3$H, —NH($C_1$-$C_8$alkyl)$OSO_3$H, —N($CH_3$)($C_1$-$C_8$ alkyl)$OSO_3$H, —O($C_1$-$C_8$ alkyl)$OSO_3$H, —NH($C_1$-$C_8$ alkyl)$PO_3H_2$, —N($CH_3$)($C_1$-$C_8$ alkyl)$PO_3H_2$, or —O($C_1$-$C_8$ alkyl)$PO_3H_2$.

Any of the definitions of $M_1$ and $M_2$ given herein in a discussion of the polymers may also be used in methods of making the polymers.

In some embodiments, the anionic Gemini surfactant has structure I(a) or I(b).

I(a)

I(b)

In some embodiments of the present disclosure, the anionic Gemini surfactant has the following structure (II):

Structure (II)

In structure (II), $X_3$ and $X_4$ are integers, each independently having a value of four to twenty; specifically four to 12, such as seven to 11, more specifically any of 4, 5, 6, or 7. $Z_1$ and $Z_2$ are integers, each independently having a value of zero, one, two, or three. In some specific embodiments of the present disclosure, $Z_1$ and $Z_2$ are zero or one. In more specific embodiments of the present disclosure, $Z_1$ and $Z_2$ are both one. Y is a covalently bound divalent linker, which is defined above in connection with structure (I). M is the counterion or a covalently bonded moiety, which is as defined above in connection with structure (I).

In some embodiments of the present disclosure, the anionic Gemini surfactant has the following structure (III):

Structure (III)

In structure (III), $X_3$ and $X_4$ are integers, each independently having a value of four to twenty; preferably four to 12, such as seven to 11, specifically seven, or specifically such as 4, 5, 6, or 7. $Z_1$ and $Z_2$ are integers, each independently having a value of zero, one, two, or three. In specific embodiments, $Z_1$ and $Z_2$ are zero or one. In specific embodiments of the present disclosure, $Z_1$ and $Z_2$ are both one. $Y_1$ is an integer having a value of two and 12, preferably between four and eight. $M_1$ and $M_2$ are as defined above in connection with structure (I).

The present disclosure is additionally directed to a method of preparing a polymerizable anionic Gemini surfactant. In some embodiments, the polymerizable anionic Gemini surfactant is prepared by contacting a carboxylic acid, a carboxylate salt, or a carboxylate ester with sufficient quantity (e.g., at least two equivalents) of a base capable of deprotonating the alpha carbon of the carboxylic acid. The carboxylic acid, carboxylate salt or carboxylate ester comprises at least one carboxylate moiety, e.g., a carboxylic acid, a carboxylate anion, or a carboxylate ester (e.g., an aliphatic ester having an aliphatic group, e.g., an alkyl group, having from one to four carbon atoms, such as methyl, ethyl, isopropyl, n-propyl, isobutyl, n-butyl, or sec-butyl) and an aliphatic group generally having at least seven carbon atoms and at least one carbon-to-carbon double bond. In some embodiments, the carbon-to-carbon double bond comprises a terminal alkene, i.e., the alkene comprises the omega carbon atom and the carbon atom bonded to the omega carbon atom. In some embodiments, the carboxylic acid comprises at least two carbon-to-carbon double bonds, such as at least two conjugated carbon-to-carbon double bonds. In some embodiments, the two conjugated carbon-to-carbon double bonds comprise terminal conjugated carbon-to-carbon double bonds. Exemplary carboxylic acids include nonenoic acid (e.g., 9-nonenoic acid), decenoic acid (e.g., 9-decenoic acid), undecenoic acid (e.g., 10-undecenoic acid), dodecenoic acid (e.g., 11-dodecenoic acid), tridecenoic acid (e.g., 12-tridecenoic acid), tetradecenoic acid (e.g., 13-tetradecenoic acid), pentadecenoic acid (e.g., 12-pentadecenoic acid), hexadecenoic acid (e.g., 15-hexadecenoic acid), oleic acid, linoleic acid, linolenic acid, stearidonic acid, eicosenoic acid, eicosatrienoic acid, arachidonic acid, rumenic acid, conjugated linoleic acid, gamma-linolenic acid, calendic acid, jacaric acid, erucic acid, nervonic acid, and the like.

The polymerizable anionic Gemini surfactant comprises at least two carboxylate groups and at least two aliphatic chains, each of the at least two aliphatic chains comprising at least seven carbon atoms and at least one carbon-to-carbon double bond, specifically at least two carbon-to-carbon double bonds, even more specifically at least two conjugated carbon-to-carbon double bonds. In one embodiment, the aliphatic chains comprise seven to 34 carbon atoms, specifically eight to 24 carbon atoms. Deprotonation of the alpha carbon of the carboxylic acid yields a carbanion that is reactive with a compound comprising leaving groups. Suitable bases include alkyl lithiums, alkylmagnesium reagents, lithium diisopropylamide, lithium tetramethylpiperidine, dialkyamide base, sodium hydride, and potassium hydride, among other suitable strong bases. The reaction suitably occurs in aprotic solvent, e.g., tetrahydrofuran, diethyl ether, an alkane solvent, an aromatic solvent, alkylamine solvents, alkyl diamine solvents, and alkyl phosphoramide solvents.

The carboxylate compound containing the reactive carbanion is then contacted with a compound comprising the Y, covalently bound divalent linker, terminated with leaving groups, which may be depicted as follows:

wherein $L_1$ and $L_2$ comprise leaving groups, and Y covalently bound divalent linker as described above. The molar ratio is generally about 2 moles deprotonated carboxylate compound to 1 mole compound containing the Y linker, but can readily be adjusted. Exemplary leaving groups include bromide, iodide, chloride, tosylate, mesylate, triflate, benzenesulfonate, and p-toluenesulfonate. This contact thereby yields the anionic Gemini surfactants of the disclosure. In some embodiments, the anionic Gemini surfactants have the structure (I), (II) or (III).

In some embodiments of the present disclosure, a polymerizable Gemini surfactant is prepared by oxidizing an anionic Gemini surfactant comprising an alkene moiety to thereby prepare terminal aldehydes, which is followed by reaction with a reagent for converting the terminal aldehydes into terminal conjugated dienes. In some embodiments, the Gemini surfactant is prepared by the above described enolate chemistry (i.e., deprotonation of the alpha carbon of a carboxylic acid, salt, or ester followed by reaction with a Y-containing compound with terminal leaving groups).

In some embodiments, a polymerizable anionic Gemini surfactant is prepared from an anionic Gemini surfactant starting material that is a dicarboxylate linked with a connecting moiety and further comprising at least two aliphatic groups, each comprising an alkene. In some embodiments, the anionic Gemini surfactant comprises at least two aliphatic groups, each comprising terminal alkenes. Such a compound may have the following general structure (IV):

Structure (IV)

wherein $X_1$, $X_2$, Y, and $R_{17}$ through $R_{22}$ are each independently hydrogen, fluoride, chloride, bromide, $C_1$ to $C_8$ alkyl, $C_2$ to $C_8$ alkenyl, tri($C_1$-$C_4$ alkyl)silyl, and substituted or unsubstituted phenyl, and $M_1$ and $M_2$ carry the definitions set forth for structures (I), (II) and (III).

In some embodiments, a Gemini dicarboxylate compound comprising aliphatic groups comprising alkenes, e.g., terminal alkenes, such as the compound depicted in structure (IV), may be contacted with an oxidizing agent to oxidize the alkene into a terminal carbonyl and thereby prepare a Gemini dialdehyde having the general structure (V):

Structure (V)

wherein $X_1$, $X_2$, Y, and $M_1$ and $M_2$ are as defined above in connection with structures (I)-(III).

The alkenes, e.g., terminal alkenes, of the Gemini dicarboxylate surfactant may be oxidized with an oxidizing agent selected from among ozone, oxygen, and metallic oxides such as metallic tetraoxides. Exemplary metallic tetraoxides include potassium permanganate ($KMnO_4$), ruthenium tetraoxide ($RuO_4$), and osmium tetraoxide ($OsO_4$). Oxidation proceeds, for example, by contacting the anionic Gemini surfactants having Structure IV with excess metal tetraoxide in any non-alcohol solvent in which the alkene is soluble. The temperature is, for example, $-100°$ C. to $+100°$ C. Oxidation with gaseous oxidants such as ozone and oxygen may be conducted in a variety of solvents in which the alkene is soluble at temperatures of $-100°$ C. to $+100°$ C.

In some embodiments, the Gemini dialdehyde is contacted with a reagent capable of converting the terminal aldehydes into terminal conjugated dienes to thereby prepare the polymerizable Gemini surfactant. The polymerizable Gemini surfactant may take either the trans or cis isomer depending upon the subsequent workup, i.e., acidic or alkaline. In general, such polymerizable Gemini surfactants have the following structures (VIa) or (VIb):

Structure (VIa)

trans isomer

Structure (VIb)

cis isomer wherein $X_1$, $X_2$, Y, and $M_1$ and $M_2$ are as defined above in connection with Structures (I), (II), and (III). The disclosure also includes polymers in which one diene is cis and the other is trans, e.g. polymers of structure (VIc)

Structure (VIc)

In some embodiments, the reagent capable of converting the terminal aldehydes into terminal conjugated dienes comprises an allylboronic acid or an ester thereof, such as a 1-trialkylsilyl)allyl-3-boronic acid or an ester thereof. In one embodiment, the allylboronic acid or ester thereof has the following structure:

wherein $R_{23}$, $R_{24}$, $R_{25}$, and $R_{26}$ are each independently hydrogen, substituted or unsubstituted alkyl, substituted or unsubstituted aryl, chelating alkyl, or aryl. $R_{23}$, $R_{24}$, $R_{25}$, and $R_{26}$ comprise 3 to 20 carbon atoms. Specific allylboronic acid esters include (1-trialkyllsilyl)allyl-3-boronic acid pinacol ester, (1-trialkylsilyl)allyl-3-boronic acid catechol ester. In some embodiments, the reagent comprises Matteson's reagent. Exemplary (1-trialkyllsilyl)allyl-3-boronic acid pinacol esters include allylboronic acid pinacol ester, allylboronic catechol ester, allylboronic acid diethyl ester, allylboronic acid 1,2-ethanediol ester, and allylboronic acid 1,3-propanediol ester.

In some embodiments, the reagent capable of converting the terminal aldehydes into terminal conjugated diene comprises a Wittig reagent or a modified Wittig reagent. In some embodiments, the Wittig reagent comprises triphenyl phosphonium ylide, having the general structure:

wherein $R_{27}$ and $R_{28}$ are each independently hydrogen, an aliphatic, e.g., alkyl, substituted alkyl, alkenyl, substituted alkenyl, alkynyl, or substituted alkynyl, or an aryl or substituted aryl. $R_{27}$ and $R_{28}$ comprise 3 to 20 carbon atoms. In some embodiments, the Wittig reagent comprises $R_{27}$ comprising —CH═CH$_2$ and $R_{28}$ comprising hydrogen. In such embodiments, the Wittig reagent may be used to prepare a terminal conjugated diene. In some embodiments, the Wittig reagent comprises $R_{27}$ comprising —CH═CH—CH═CH$_2$ and $R_{28}$ comprising hydrogen. In such embodiments, the Wittig reagents may be used to prepare a terminal conjugated triene.

In some embodiments, the reagent capable of converting the terminal aldehydes into terminal conjugated diene comprises a phosphonate carbanion. In some embodiments, the reagent has the general structure:

wherein $R_{29}$ and $R_{30}$ are each independently hydrogen, an aliphatic, e.g., alkyl, substituted alkyl, alkenyl, substituted alkenyl, alkynyl, or substituted alkynyl, or an aryl or substituted aryl. $R_{29}$ and $R_{30}$ comprise 3 to 20 carbon atoms. EWG is an electron withdrawing group and may provide the conjugated alkenyl moiety. In some embodiments, the phosphonate carbanion reagent comprises EWG comprising $R_{29}$ comprising —CH=CH$_2$ and $R_{30}$ comprising hydrogen. In such embodiments, the phosphonate carbanion reagent may be used to prepare a terminal conjugated diene. In some embodiments, the reagent comprises the Horner-Wadsworth-Emmons reagent.

Contact with the reagent, suitably, an allylboronic acid or ester thereof, is followed by an elimination reaction, e.g., a silanol elimination reaction. The use of other reagents, e.g., Wittig type reagents or phosphonate carbanions, involve eliminations of the phosphorus-containing moieties. The pH of the elimination reaction influences the isomerism of the final polymerizable Gemini surfactant. An acidic workup (e.g., sulfuric acid in tetrahydrofuran) generally yields substantially more trans isomer than cis, such as at least about 60:40 trans:cis, at least about 80:20 trans:cis, at least about 90:10 trans:cis, or even at least about 95:5 trans:cis. An alkaline workup (e.g. potassium hydroxide in tetrahydrofuran) generally yields substantially more trans isomer than cis, such as at least about 60:40 cis:trans, at least about 80:20 cis:trans, at least about 90:10 cis:trans, or even at least about 95:5 cis:trans.

In some embodiments, the present disclosure is directed to a polymer comprising a cross-linked or polymerized anionic Gemini surfactant. The anionic Gemini surfactant comprises at least two carboxylate moieties and at least two aliphatic moieties. Additionally, at least two of the aliphatic chains comprise at least seven carbon atoms and at least one pair of conjugated carbon-to-carbon double bonds. In some embodiments, the polymerizable anionic Gemini surfactant according to the present disclosure has the structure (I):

wherein $X_1$, $X_2$, Y, $M_1$, $M_2$, $Z_1$, $Z_2$, and $R_1$ through $R_{10}$ are as defined above. The polymer comprising the polymerized anionic Gemini surfactant is thus polymerized from an anionic Gemini surfactant having structure (I). The polymer comprises 1 to $10^{25}$, 10 to $10^{23}$, 10 to $10^{15}$, 10 to $10^6$, or 10 to $10^4$ units of the anionic Gemini surfactant. In some embodiments the surfactant is any one of the following:

In some embodiments, the polymer comprises a cross-linked anionic Gemini surfactant polymerized from an anionic Gemini surfactant having any of structures (II), (III), (VIa), (VIb), and (VIc) all as described above.

The polymerized anionic Gemini surfactant may be in a form of a porous polymer film. The present disclosure is therefore further directed to a polymer, which may be in the form of a porous polymer film or membrane comprising polymerized anionic Gemini surfactants according to the present disclosure. In some embodiments, the present disclosure provides bulk materials comprising polymers formed from the anionic Gemini surfactants of the present disclosure. The polymers may be formed in nearly any dimension or geometry. In some embodiments, the thickness of the membrane or bulk material may be about 1 micrometers to about 5 millimeters, such as about 10 micrometers to about 5 millimeters.

The membranes may formed as a film between two plates (the plates may be transparent if cross-linking is achieved through photopolymerization), or may be formed on or within a porous support. The support may be of a suitable material known to those skilled in the art including polymers, metals, and ceramics. In some embodiments, the support is a porous polymeric material. In some embodiments, the porous support is polyethylene (including high molecular weight and ultra-high molecular weight polyethylene), polyacrylonitrile (PAN), polyacrylonitrile-co-polyacrylate, polyacrylonitrile-co-methacrylate, polysulfone (Psf), Nylon 6, 6, poly(vinylidene difluoride) or polycarbonate. Methods for forming composite membranes comprising polymers according to the present disclosure attached to a porous support are described in PCT/US2003/031429 and U.S. Patent Application Publication US 2006/0096922 by Gin et al., hereby incorporated by reference for their disclosure of methods to form composite membranes. In some embodiments, the composite membrane comprising polymerized anionic Gemini surfactant and a porous support may be prepared by applying anionic Gemini surfactant monomer to the support followed by polymerization. Solvents may include organic solvent, water, or another polar solvent; and an optional polymerization initiator. Application of the solution to the support can be achieved by any solution based process known to the art, including painting, rolling, spraying and inkjet printing of the solution onto the support. The solution is applied to form a coating on at least a portion of the surface of the support. The solvent may be evaporated from the film by allowing the solvent to evaporate at ambient temperature. Temperatures and controlled atmospheres as known by those skilled in the art can be used to evaporate the solvent from the film.

In some embodiments, the polymer comprising polymerized Gemini surfactants is formed on network glasses, particularly silicate glass, fluoride glass, aluminosilicates, phosphate glasses, borate glasses, and chalcogenide glass. The polymer comprising polymerized Gemini surfactants may be formed on metal substrates, e.g., copper, aluminum, zinc, etc. for use as, for example, ion transport films in batteries.

In some embodiments, the polymerized Gemini surfactants may be polymerized into a cross-linked network with substantial retention of the original LLC phase microstructure. In some embodiments, the present disclosure provides polymer membranes comprising lyotropic liquid crystal polymers formed from the anionic Gemini surfactants of the present disclosure. That is, the anionic Gemini surfactants may be mixed with a suitable solvent to thereby prepare a lyotropic liquid crystal phase, which may then be polymerized. The solution to prepare the lyotropic liquid crystal may optionally further contain a polymerization initiator. Some embodiments of the present disclosure are directed to polymerized anionic Gemini surfactant in a form of a triply periodic multiply continuous lyotropic phase. In some embodiments, the triply periodic multiply continuous lyotropic phase comprises a gyroid phase (space group #230). In some embodiments, the triply periodic multiply continuous lyotropic phase comprises a double diamond phase (space group #224). In some embodiments, the triply periodic multiply continuous lyotropic phase comprises a primitive cubic phase (space group #229). In some embodiments, the triply periodic multiply continuous lyotropic phase comprises a hexagonal tetracontinuous phase (space group #193) (space group #193) with percolating pores in three dimensions.

The present disclosure is further directed to a lyotropic liquid crystal composition prepared by polymerizing a polymerizable anionic Gemini surfactant having an LLC phase. The LLC phase may be prepared by combining a polymerizable anionic Gemini surfactant according to the present disclosure and a suitable polar solvent, preferably a polar, protic solvent. Exemplary polar solvents, including polar, protic solvents, are selected from water, ethylene glycol, diethylene glycol, glycidol, 2-butene-1,4-diol, propanediol, glycerol, formamide, N-methylformamide, N,N-dimethylformamide, N-ethylformamide, acetamide, N-methylacetamide, N-ethylacetamide, methanol, ethanol, propanol, ethylammonium nitrate, ethanolammonium nitrate, ethyl ammonium formate, ethanolammonium formate; ethylammonium acetate, ethanolammonium acetate, 1-ethyl-3-methyl-imidazolium acetate, 1-ethyl-3-methyl-imidazolium bis(trifluoromethylsulfonyl)imide, 1-ethyl-3-methylimidazolium tetrafluoroborate, or any combination thereof, with water being particularly preferred. The lyotropic liquid crystal composition of the present disclosure prepared by combining a polymerizable anionic Gemini surfactant and polar, protic solvent are capable of robustly forming a variety of lyotropic liquid crystal phases. The polymerizable anionic Gemini surfactants of the present disclosure are capable of forming triply periodic multiply continuous phases over a broad range of concentrations and temperatures. These triply periodic multiply continuous phases encompass bicontinuous cubic phases known in the art, for example, the gyroid phase (space group #230), double diamond phase (space group #224), or primitive cubic phase (space group #229). The triply periodic multiply continuous phases of the present disclosure additionally encompass tetracontinuous phases, such as a novel hexagonal tetracontinuous phase (space group #193) with percolating pores in three dimensions. The pores in these materials may range from 5-100 Å. See FIG. 1.

In some embodiments, the polymerizable anionic Gemini surfactant forms a triply periodic multiply continuous phase such as a gyroid phase (space group #230), double diamond phase (space group #224), primitive cubic phase (space group #229), or hexagonal tetracontinuous phase (space group #193) over a range of concentrations from $C_i$ to $C_{ii}$ wherein the difference between $C_i$ and $C_{ii}$ is at least 10 weight percent, at least 12 weight percent, at least 14 weight percent, at least 16 weight percent, at least 18 weight percent, or at least 20 weight percent. Advantageously, the three dimensional multiply continuous phase is stable over a broad range of temperatures from $T_i$ to $T_{ii}$ wherein the difference between $T_i$ and $T_{ii}$ is at least 40° C., at least 45° C., at least 50° C., at least 55° C., at least 60° C., at least 65° C., at least 70° C., at least 75° C., or at least 80° C.

According to empirical results to date, the polymerizable anionic Gemini surfactant forms a triply periodic multiply continuous phase at concentrations of at least 5 weight percent, specifically at least 10 weight percent. In some embodiments, the concentration of the polymerizable anionic Gemini surfactant are higher, such as at least 40 weight percent, at least 45 weight percent, or at least 50 weight percent. At these concentrations, the lyotropic liquid crystal phase generally transitions from hexagonal to Q-phase. At anionic Gemini surfactant concentrations generally no greater than 90 weight percent, no greater than 85 weight percent, or no greater than 80 weight percent, the lyotropic liquid crystal phase generally transitions from Q-phase to lamellar. The concentrations at which these phase transitions occur depend upon multiple factors, in addition to concentration. These factors include the structure of the anionic Gemini surfactant, the identity of the counterion, the temperature of the system, the pressure of the system, and the presence and identity of co-solvents, if any are added to the system. In view thereof, the concentrations of the phase transition may vary significantly from one surfactant to another. The anionic Gemini surfactants comprising at least one, and specifically two, carboxylate groups of the present disclosure advantageously provide robust LLC systems exhibiting triply periodic multiply continuous phases over broad concentration and temperature ranges.

The solvent concentration is generally at least 5 weight percent, specifically at least 10 weight percent, in order to prepare a lyotropic liquid crystal. At concentrations less than about 5 weight percent or less than about 10 weight percent, the anionic Gemini surfactant generally forms a crystalline phase. In specific embodiments, the solvent is water. The solvent optionally includes additional solvents, generally in low concentrations, such as less than 10 weight percent, specifically less than 5 weight percent. For example, the surfactant may be introduced into the LLC phase pre-dissolved in a solvent in which the surfactant is soluble. Suitable solvents for pre-dissolving the surfactants may include methanol, ethanol, acetone, tetrahydrofuran, diethyl ether, glycerol, ethylene glycol, dimethylformamide, and combinations thereof.

The polymers of the present disclosure, which include lyotropic liquid crystal compositions, comprising polymerizable anionic Gemini surfactants may be polymerized by chemically crosslinking the polymerizable anionic Gemini surfactant with a suitable polymerization agent. In some embodiments wherein a lyotropic liquid crystal structure is to be retained, the polymerizable anionic Gemini surfactant to be polymerized by chemical crosslinking may be any of the liquid crystal phases, e.g., hexagonal, lamellar, micellar, and even the three dimensional multiply continuous phases including the gyroid, double diamond, primitive, and hexagonal tetracontinuous phase (space group #193) with percolating pores.

In some embodiments, a polymerizable Gemini surfactant, which may be contained within a lyotropic liquid crystal, is contacted with a crosslinking agent such as a photoinitiator. The photoinitiator is present in the mixture of Gemini surfactant and solvent, which thereby causes formation of the LLC phase. Exemplary photoinitiators are substituted acetophenones, such as 2,2-dimethoxy-2-phenylacetophenone, 2,2-diethoxyacetophenone, 2-benzyl-2-(dimethylamino)-4'-morpholinobutyrophenone, 4'-tert-butyl-2',6'-dimethylacetophenone, diphenyl(2,4,6-trimethylbenzoyl)phosphine oxide/2-hydroxy-2-methylpropiophenone, 4'-ethoxyacetophenone, 3'-hydroxyacetophenone, 1-hydroxycyclohexyl phenyl ketone, 2-hydroxy-4'-(2-hydroxyethoxy)-2-methylpropiophenone, 2-hydroxy-2-methylpropiophenone, 2-Methyl-4'-(methylthio)-2-morpholinopropiophenone, 4'-phenoxyacetophenone, and combinations thereof.

In one embodiment, the polymer is prepared by irradiating the polymerizable Gemini surfactant to photoinitiate crosslinking of the polymerizable surfactants and thereby fix the lyotropic liquid crystal into a stable, robust structure. The lyotropic liquid crystal may be irradiated with light having a wavelength dependent upon the photoinitiator selected. In general, the wavelength is 220 nm to 600 nm.

In some embodiments, a polymerizable Gemini surfactant, which may be contained within a lyotropic liquid crystal, is contacted with a crosslinking agent such as a thermal initiator. In this embodiment, the thermal initiator is present in the mixture of Gemini surfactant and solvent, which thereby causes formation of the LLC phase. Suitable thermal initiators include azo initiators such as azobisisobutyronitile (AIBN), 1,1'-azobis(cyclohexane-1-carbonitrile) (V-40), 2,2'-azobis(4-methoxy-2.4-dimethyl valeronitrile) (V-70), 2,2'-azobis(2.4-dimethyl valeronitrile) (V-65), dimethyl 2,2'-azobis(2-methylpropionate) (V-601), 2,2'-azobis (2-methylbutyronitrile) (V-59), 2,2'-azobis[N-(2-propenyl)-2-methylpropionamide] (VF-096), 1-[(1-cyano-1-methylethyl)azo]formamide (V-30), 2,2'-azobis(N-butyl-2-methylpropionamide) (VAm-110), and 2,2'-azobis(N-cyclohexyl-2-methylpropionamide) (VAm-111). Additional azo initiators include 2,2'-azobis[2-(2-imidazolin-2-yl)propane] (VA-061), 2,2'-azobis{2-methyl-N[1,1-bis(hydroxymethyl)-2-hydroxyethyl]propionamide} (VA-080), and 2,2'-azobis[2-methyl-N-(2-hydroxyethyl)propionamide] (VA-086). Combinations of the foregoing azo initiators are also included. The temperature of thermal initiation depends upon the specific initiator used. In general, thermal initiation may occur at temperatures of 22° C. to 150° C., specifically 60° C. to 120° C.

Other exemplary initiators include peroxides, such as alkyl, dialkyl, aryl, and diaryl peroxides. In this embodiment, the peroxide is present in the mixture of Gemini surfactant and solvent, which thereby causes formation of the LLC phase. Exemplary peroxides include tert-butyl peroxide, di-tert-butyl peroxide, benzyl peroxide, lauroyl peroxide (LUPEROX™), methyl ethyl ketone peroxide, acetone peroxide, and benzoyl peroxide. Peroxides are also thermal initiators which work at temperatures of 22° C. to 150° C., specifically 60° C. to 120° C.

In some embodiments, a polymerizable Gemini surfactant may be crosslinked by ionizing radiation (X-rays or gamma rays), without the aid of a chemical crosslinking agent. Ionizing radiation having a wavelength of about 1 nm to about $10^{-5}$ nm is generally suitable for crosslinking.

Current empirical results to date indicate that lyotropic liquid crystals comprising polymerized Gemini surfactants exhibit enhanced long range order compared to lyotropic liquid crystals known in the art. The long range order is demonstrated by multiple peaks in X-ray diffraction patterns obtained from the thin films of the present disclosure. X-ray diffraction patterns obtained to date exhibit multiple peaks, generally in excess of four peaks, five peaks, six peaks, seven peaks, or even eight peaks, thereby showing the retention of long range order in the thin films of the present disclosure.

The following examples illustrate specific embodiments with the scope of the present disclosure. The examples are provided for the purpose of illustration and are not to be construed as limitations of the present disclosure.

Example 1

Synthesis of Polymerizable Anionic Gemini Surfactant

The cross-linkable Gemini surfactant potassium 2,9-di ((E)-undeca-8,10-dieny-1-yl)decanedioate was synthesized as shown in Scheme 1. The lithium enolate of 10-undecenoic acid (2 equiv.) was coupled with 1,6-dibromohexane (1 equiv.) to furnish 1 with a Gemini structure bearing terminal double bonds. Esterification of 1 with MeOH was achieved under acidic conditions to furnish a Gemini diester, which was ozonolyzed to yield Gemini diester dialdehyde 2. Treatment of 2 with Matteson's reagent, followed by an exposure to $H_2SO_4$ effected the one-pot installation of the unsaturated dienes on both tails of the diester in 3. Basic hydrolysis of the methyl esters in 3 furnishes the unsaturated Gemini diacid, which was neutralized with $K_2CO_3$ to yield the desired cross-linkable Gemini surfactant 4.

Scheme 1.

This cross-linkable anionic Gemini surfactant forms lyotropic liquid crystals having the following structures from 30 wt. % to 100 wt. % in 5 wt. % increments:

35 to 55 wt. % hexagonal
55 to 65 wt. % gyroid
65 to 75 wt. % lamellar
75 to 95 wt. % primitive mesophase.

Example 2

Polymerizing a Polymerizable Anionic Gemini Surfactant

Figure 3:
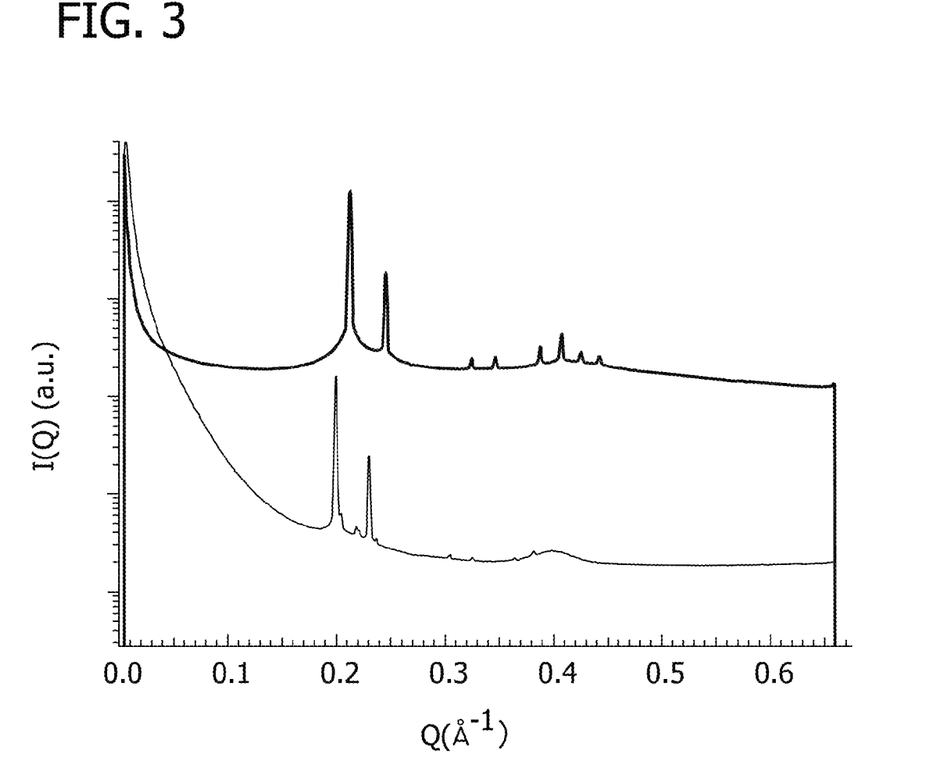
FIG. 3 depicts azimuthally integrated X-ray diffraction patterns of a lyotropic liquid crystal (LLC) based on 65 wt % 4, 0.4 wt % 2,2-dimethoxy-2-phenylacetophenone, and 34.6 wt % H$_2$O. The LLC was prepared as set forth in Example 2. The polymerizable surfactant forms a gyroid phase before UV crosslinking (bottom curve). The XRD of the LLC after UV crosslinking polymerization (upper curve) demonstrates retention of the gyroid morphology with a slight reduction in the unit cell dimensions.

The unsaturated Gemini surfactant 4 (65 wt %) was combined with the free radical photoinitiator 2,2-dimethoxy-2-phenylacetophenone (0.4 wt %) and water (34.6 wt %) to yield a lyotropic liquid crystal (LLC). X-ray diffraction analyses ($Q^{230}$ of the resulting gel demonstrated that this LLC adopts a stable gyroid phase space group symmetry) as shown in FIG. 3. FIG. 3 depicts azimuthally integrated X-ray diffraction patterns of a lyotropic liquid crystal (LLC) based on 65 wt % 4, 0.4 wt % 2,2-dimethoxy-2-phenylacetophenone, and 34.6 wt % $H_2O$. The polymerizable surfactant forms a gyroid phase before UV crosslinking (bottom curve). The XRD of the LLC after UV crosslinking (upper curve) demonstrates retention of the gyroid morphology with a slight reduction in the unit cell dimensions.

Figure 4:
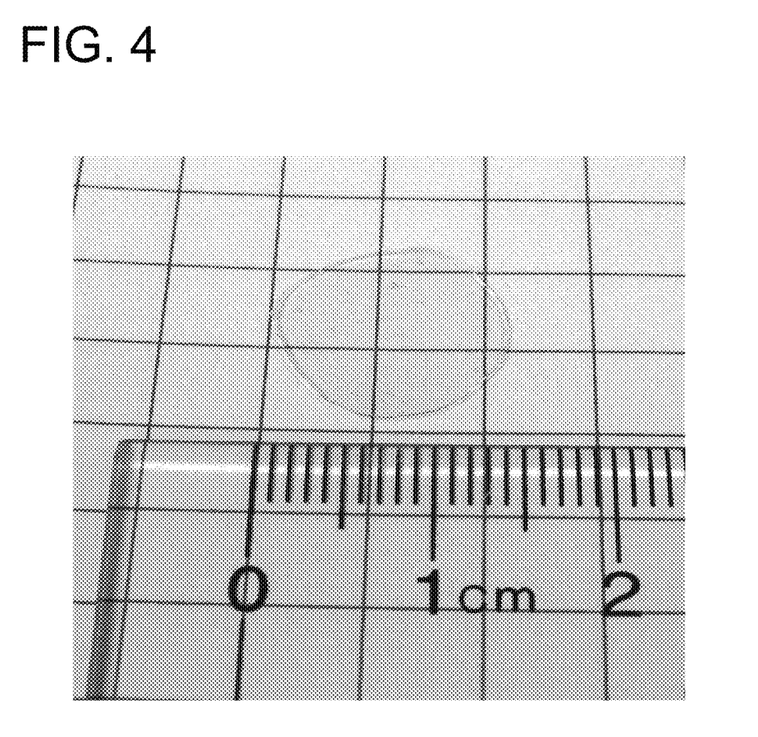
FIG. 4 is an optical micrograph of the film resulting from UV crosslinking of the LLC derived polymerizable Gemini surfactant 4.

The gel was crosslinked by the following protocol. The stiff LLC gel was pressed between two circular quartz plates with a Teflon spacer (<2 mm thickness) to yield a flat gel with near constant thickness, and this sandwich geometry was secured using 2-3 binder clips to mitigate water loss. The sample sandwich was placed on a heating block thermostatted at 50° C. and irradiated for 1 hour, using a UV lamp (Ultra Violet Products UVGL-15) with a peak wavelength of 365 nm that was placed 1 cm above the top of the sample. Upon cooling to room temperature and disassembly of the sample sandwich, a crosslinked film was isolated as ascertained by its complete insolubility in water. See FIG. 4.

The morphology of the resulting film was analyzed by X-ray diffraction and shown to retain the gyroid structure with a slight reduction in the size of the unit cell. See FIG. 3. The long-range structural order of the crosslinked gyroid phase is exhibited by the eight scattering maxima in the XRD patterns for this film.

A dash ("-") that is not between two letters or symbols is used to indicate a point of attachment for a substituent. For example, —$(CH_2)C_3$-$C_8$cycloalkyl is attached through carbon of the methylene ($CH_2$) group.

The term "substituted", as used herein, means that any one or more hydrogens on the designated atom or group is replaced with a selection from the indicated group, provided that the designated atom's normal valence is not exceeded. "Optionally substituted" means substituted or unsubstituted. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture. Unless otherwise specified substituents are named into the core structure. For example, it is to be understood that when (cycloalkyl)alkyl is listed as a possible substituent the point of attachment of this substituent to the core structure is in the alkyl portion.

Suitable groups that may be present on a "substituted" position include, but are not limited to, e.g., halogen; cyano; hydroxyl; nitro; azido; —COOH, —$SO_3H$, amino, —(C=O)$NH_2$, alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxyl, alkyl, alkoxy, halogen and amino.

As used herein, when a definition is not otherwise provided, "substituted" indicates replacement of one or more hydrogen atoms of a group with a substituent selected from a $C_1$ to $C_6$ alkyl group, a $C_1$ to $C_6$ hydroxyalkyl group, a $C_2$ to $C_6$ alkenyl group, a $C_2$ to $C_6$ alkynyl group, a aryl group, a 5-7-membered heteroalkyl group, a $C_3$-$C_7$ cycloalkyl group, a $C_3$ to $C_7$ cycloalkenyl group, a cycloalkynyl group, a heterocycloalkyl group, halogen (Br, F or Cl), a haloalkyl group, an alkoxy group, a halogen (F, Cl, Br, or I), a hydroxyl group (OH), an acid group (—COOH), —$PO_3H_2$, —$SO_3H$, —$OSO_3H$, a nitro group (—$NO_2$), a cyano group (—CN), an amino group (—$NR'_2$ wherein each R' is independently a hydrogen or a $C_1$ to $C_6$ alkyl group), a carbonyl group (—C(=O)—), a carbamyl group, or an ester group (—C(=O)OR" wherein R" is a $C_1$ to $C_6$ alkyl group or a $C_6$ to $C_{10}$ aryl group), a carboxyl group (—C(=O)OH) or a salt thereof, and a combination thereof.

An "aliphatic group" is organic chemical group in which the carbon atoms are linked in open chains, such as alkanes, alkenes and alkynes. An aliphatic group may be branched or unbranched and may also be a non-aromatic cyclic group such as a cyclohexyl or cyclohexenyl group or may include both cyclic and acyclic groups. An aliphatic group may be entirely hydrocarbon (hydrocarbyl) in composition or may be substituted with non-hydrocarbon substituents. An "alkyl" group is a straight or branched chain saturated aliphatic hydrocarbyl group having the specified number of carbon atoms, a valence of one, and optionally substituted with one or more substituents where indicated.

An "alkenyl" group is a straight or branched chain hydrocarbyl group having the specified number of carbon atoms, a valence of one, at least one carbon-carbon double bond, and optionally substituted with one or more substituents where indicated.

An "alkynyl" group is a straight or branched chain hydrocarbon having the specified number of carbon atoms a valence of one, at least one carbon-carbon triple bond, and optionally substituted with one or more substituents where indicated.

"Amino acid side chains" include, but are not limited to, the side chains of the 20 common naturally occurring amino acids, e.g.

In certain embodiments "amino acid side chain" does not include the proline side chain.

A "cycloalkyl" group is a hydrocarbyl group having one or more saturated rings in which all ring members are carbon, the specified number of carbon atoms, a valence of one, and optionally substituted with one or more substituents where indicated. Non-limiting examples include cyclopropyl, cyclobutyl, cyclopentyl, cyclohexyl, cycloheptyl, cyclooctyl, and adamantly groups. Cycloalkyl groups do not contain an aromatic ring or a heterocyclic ring.

An "aryl" group is a carbocyclic ring system that includes one or more aromatic rings in which all ring members are carbon, having the specified number of carbon atoms, a valence of one, and optionally substituted with one or more substituents where indicated and having. More than one ring may be present, and any additional rings may be independently aromatic, saturated, or partially unsaturated and multiple rings, if present, may be fused, pendent, spirocyclic or a combination thereof. Non-limiting examples include phenyl, naphthyl, and tetrahydronaphthyl groups. "Phenyl" means a six-membered aromatic ring.

"Heteroaryl" indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

A "heterocyclic ring" is a saturated, unsaturated, or aromatic ring group having at least one ring containing a heteroatom chosen from N, O, and S, with remaining ring atoms being carbon.

Examples of heterocyclic rings include pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

As used herein, when a definition is not otherwise provided, the prefix "hetero" means that the group has 1 to 3 heteroatoms independently selected from N, O, S, P Si, and B, and a combination thereof. "Heteroaliphatic" includes an aliphatic group as defined herein, with at least on heteroatom in the aliphatic chain. In cyclic groups, 1 to 3 heteroatoms can be present as a ring member. For example, a pyridyl is C5 heteroaryl group, and an "alkoxy" group is a heteroalkyl group where an alkyl moiety is linked via an oxygen (e.g., methoxy). In a cyclic group the following heteroatoms may be used: N, O, and S.

While the stereochemistry of the various compounds is not explicitly shown, it is to be understood that this disclosure encompasses all isomers.

When referring to the molecular weight of a polymer, the term molecular weight refers to number-averaged molecular weight ($M_n$).

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to various embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

What is claimed is:
1. A polymerizable Gemini surfactant having the following structure:

wherein $X_1$ and $X_2$ are each independently an optionally substituted aliphatic group having from four to 30 carbon atoms;

$Z_1$ and $Z_2$ are integers, each independently having a value of one, two, or three;

Y is a covalently bound divalent linker, and is a $C_3$-$C_{20}$ substituted or unsubstituted, aliphatic or heteroaliphatic linker;

$M_1$ and $M_2$ are the same and are each independently selected from hydroxyl, —$OR_{11}$, and —$O^-(M^+)$ where $M^+$ is a counterion, wherein $R_{11}$ is $C_1$-$C_4$ alkyl; and $R_1$ through $R_{10}$ are each independently chosen from hydrogen, fluoride, chloride, bromide, $C_1$-$C_8$ alkyl, $C_2$-$C_8$ alkenyl, tri($C_1$-$C_4$ alkyl)silyl, and substituted or unsubstituted phenyl, wherein $R_1$ and $R_6$ are the same, $R_2$ and $R_7$ are the same, $R_3$ and $R_8$ are the same, $R_4$ and $R_9$ are the same and $R_5$ and $R_{10}$ are the same.

2. The surfactant of claim 1, wherein $Z_1$ and $Z_2$ each have a value of one.

3. The surfactant of claim 1, having the structure:

wherein $X_3$ and $X_4$ are integers, each independently having a value of four to twenty.

4. The surfactant of claim 3, wherein $X_3$ and $X_4$ each independently have a value of four to 12.

* * * * *